United States Patent [19]

Cornale et al.

[11] Patent Number: 5,044,014
[45] Date of Patent: Sep. 3, 1991

[54] EAR COVERING APPARATUS

[76] Inventors: Michael A. Cornale, 1-47 Stanley Street, Hamilton, Ontario, Canada, L9H 2K9; Michael A. Cornale, 24 Highland Park Dr., Hamilton, Ontario, Canada, L9H 3L9

[21] Appl. No.: 577,577
[22] Filed: Sep. 5, 1990
[51] Int. Cl.⁵ .............................................. A61F 11/14
[52] U.S. Cl. ............................................. 2/209; 2/423
[58] Field of Search ................... 2/423, 209, 208, 410, 2/425; 128/857, 864, 866, 867, 868

[56] References Cited

U.S. PATENT DOCUMENTS

| | | | |
|---|---|---|---|
| 2,782,423 | 2/1957 | Simon et al. | 2/423 |
| 3,593,341 | 7/1971 | Aileo | 2/209 |
| 4,682,374 | 7/1987 | Geiser | 2/209 |
| 4,821,345 | 4/1989 | Marchello | 2/209 |
| 4,872,219 | 10/1989 | Duncan | 128/866 |
| 4,958,697 | 9/1990 | Moody | 2/423 |

FOREIGN PATENT DOCUMENTS 338463 10/1989 European Pat. Off. ............... 2/423

Primary Examiner—Werner H. Schroeder
Assistant Examiner—Amy Brooke Vanatta
Attorney, Agent, or Firm—Donald E. Hewson

[57] ABSTRACT

An ear covering apparatus for improving the hearing of a person in a rearward direction is disclosed. The apparatus is shaped so as to have a front, a first side, a top, and a bottom and to be open at the opposite side and the rear. The apparatus is worn over the ear such that a concavity is formed between the ear and the apparatus. The opening at the rear is located behind the ear. Further, the apparatus is shaped so as to reflect sound from a rearward direction to the ear. The apparatus also employs a slot in the side for reducing air pressure within the apparatus and thus increasing the level of sound reaching the ear.

14 Claims, 1 Drawing Sheet

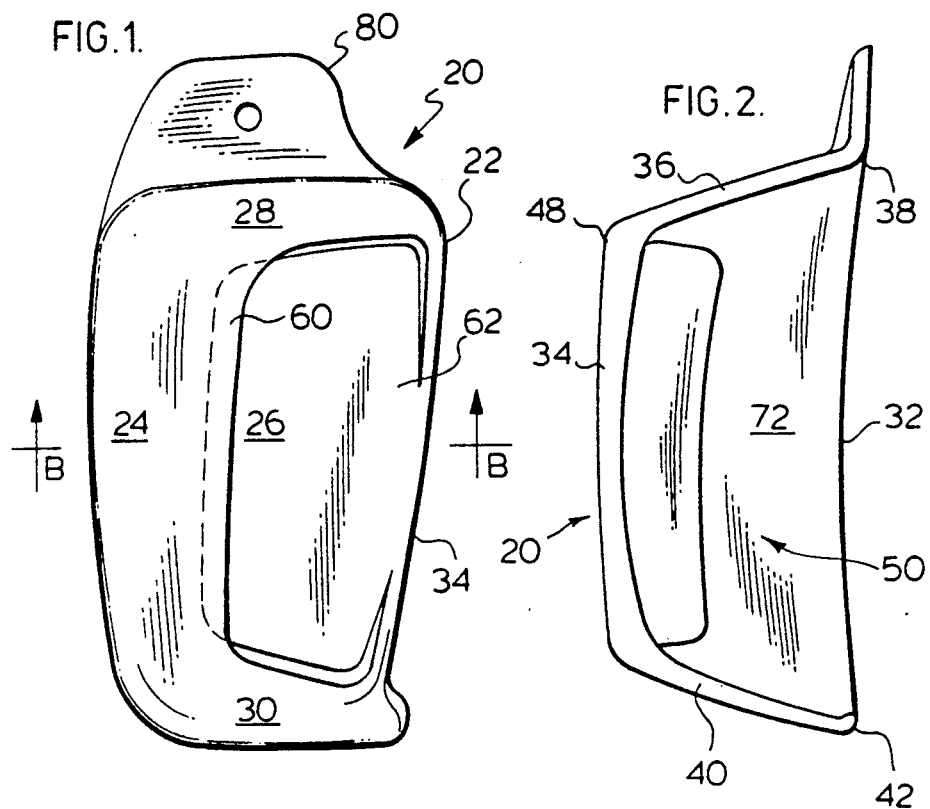
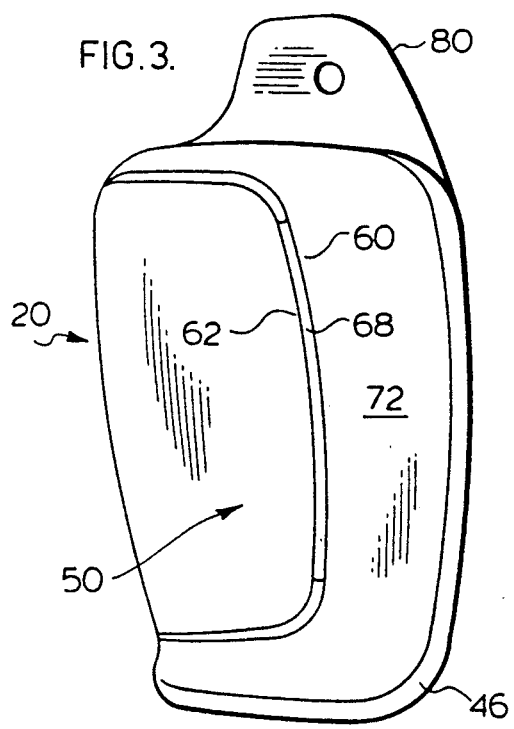
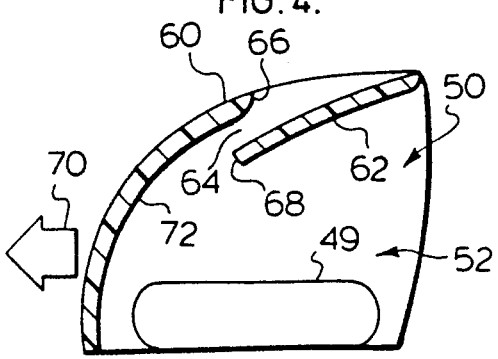

EAR COVERING APPARATUS

FIELD OF THE INVENTION

This invention relates to devices for covering a wearer's ear or ears in an attempt to control noise, and more particularly to devices for amplifying the sound from a certain direction while attenuating sound from other directions and noise in general. In situations where wind is present, precluding wind noise is also important. Examples of situations where such a device would be used include riding a bicycle or jogging. Indeed, the device could be used in virtually any sport or situation where the wearer would benefit by hearing sound coming from behind.

BACKGROUND OF THE INVENTION

There are many situations, such as in sports, transportation, on construction sights, and so on, where it is very difficult to discriminate between noise and sounds that a person wishes to hear. Resultingly, the noise effectively masks the sound and the sound is never heard. The noise may be ambient noise or may be as a result of air flow past the ears, which could be caused by wind or by motion of a person through the air, such as when riding a bicycle.

Since both ambient noise and noise from air flow past the ear contribute to the overall noise level experienced by a person, any situation that typically includes both of these sources of noise is a prime candidate for controlling the noise level around a person's ears. Further, in a situation where it is important that certain sounds be heard, the prevention and attenuation of noise and the amplification of these certain sounds is almost essential. Indeed, in some situations, it may be very dangerous to not hear certain sounds, and both ambient noise and air flow noise must be precluded from reaching the ear and the desired sounds should be amplified if possible.

One such situation occurs when a person is riding a bicycle. The noise experienced while riding a bicycle is caused largely by wind noise and also to some degree by ambient noise. It is also very important that certain sounds be heard, especially the sound of a vehicle approaching from the rear, since not hearing such sounds might cause a dangerous situation.

There are several million people in North America who regularly ride bicycles, whether for fun, for transportation purposes, for exercise, in athletic competition, or for whatever reason. While it is possible that in many places bicycles may be ridden on paths, lanes, or streets especially designated for bicycles, or at least where there are no motor vehicles, it is far more common that bicycles are ridden on roadways shared by motor vehicles. As such, it is nesessary that bicycles observe the rules of the road. In order to be within the rules of the road it is necessary that a cyclist ride on the same side of the road as a motor vehicle would travel on.

With having to share the road with cars, trucks, and the like, all of which are many times heavier and travel much faster than bicycles, safety becomes a very great concern for cyclists. This is especially true since any vehicle approaching a bicycle as it moves along the road would be approaching from the rear, which makes it very difficult to observe a motor vehicle as it approaches. Indeed, most motor vehicles go unnoticed until they are very close behind a cyclist. Typically, the first clue that a cyclist has that a vehicle is approaching very closely is the noise from the vehicle. Unfortunately, by the time a cyclist can hear or see a vehicle approaching, the vehicle is usually quite close behind or even directly beside the cyclist. Tests have shown that an average distance for being able to hear a vehicle approaching from behind is in the order of forty feet. This entire problem is exacerbated on roads where a cyclist may be travelling quickly, such as a highway or a country road, because of the increased wind noise in the cyclist's ear. Furthermore, on such roads, vehicles tend to travel faster and therefore the time between when they can first be heard and when they reach a cyclist is very minimal, in the order of one second or even half a second. Such a situation may be very dangerous given that the cyclist can not prepare for the approaching vehicle.

Such a situation could also occur in other types of activities such as running along roads, or even in unrelated events such as sports or construction sites where it may be nesessary to hear something from behind. Such sports might include sailing, football, hockey, bobsledding, and the like.

DESCRIPTION OF THE PRIOR ART

The prior art includes such things as cotton placed in one's ears, or properly designed earplugs. Such ear plugs are designed to attenuate sound that is at relatively high frequencies typically found in noise, being such that they allow lower frequency sounds such as usually found in voices to pass. Placement of such objects in one's ears may cut down on the ambient noise heard by the wearer, but also would cut down on any sound that the wearer desires to hear.

In the specific situation of a bicycle cyclist, rear view mirrors may be considered prior art in that they allow the cyclist to know what is behind him. This is a poor solution in that it is necessary to keep looking in the mirrors on a regular basis, when actually it is most desirable to be looking forwardly at all times. Mirrors are considered by most cyclists as an unsatisfactory solution to knowing what is approaching behind. It is also very possible that a vehicle could approach from behind fairly quickly when a cyclist is not looking in the mirror. Hearing a vehicle approaching from behind is by far preferable since it is done involuntarily with no interruption of safe cycling procedures.

SUMMARY OF THE INVENTION

The present invention provides an apparatus to he worn over one or both ears in order to improve hearing in a rearward direction, and at the same time does not substantially reduce hearing in other directions. The apparatus accomplishes this by fitting over the ear in such a way that sound waves and wind are substantially blocked out from the front, top and bottom, with sound being permitted to enter from the rear.

The apparatus may also incorporate at least one pair of overlapping louvers and a slot therebetween, which combine to direct air flow in such a manner that noise due to air flow around the apparatus is generally precluded, when the apparatus is in proper position over the ear. Such louvers are very useful in precluding noise due to air flow. In situations where there is no air flow over the apparatus, such louvers may be of minimal or no benefit.

Furthermore, the apparatus is of a shape that directs sounds entering it from the rear towards the ear. In order to do this, the interior of the apparatus is shaped so as to reflect sound waves toward the opening of the ear. Typically, a parabolic shape is used for this purpose.

It is a basic object of the present invention to provide an apparatus for wearing over one's ear, that allows the person to hear sounds coming from a rearward direction better than with a normal unaided ear.

It is another object of the invention to provide an apparatus for wearing over one's ear, that precludes the noise caused by air flow over the ear and also precludes noise caused by air flow over the apparatus itself.

Experimental data show a remarkable improvement in hearing when using the apparatus as opposed to hearing with the unaided ear. The experiment was performed in the following manner. A bicycle was ridden at a substantially constant given speed along a stretch of paved country road. A vehicle approached the bicycle and rider from behind, also at a substantially constant given speed that was somewhat higher. Both the rider and vehicle driver were carrying a visible flag in one hand. When the rider could hear the vehicle he would drop the flag. When the vehicle driver saw the flag drop, he would drop his flag. The distance between the flags was then measured to indicate the distance that the vehicle was behind the bicycle when the rider first heard the vehicle.

The experiment was performed several times with two different riders and two different drivers. Consistant results were obtained independent of the driver or the rider. The average distance at which the vehicle could be heard with an unaided ear was 40 feet, and with the ear covering apparatus of the present invention in place, it was 248 feet. This difference represents a 520% improvement, which is an extremely significant improvement.

BRIEF DESCRIPTION OF THE DRAWINGS

Embodiments of this invention will now be described by way of example in association with the accompanying drawings, in which:

FIG. 1 is a side view of ear covering apparatus;

FIG. 2 is a rear view of the apparatus shown in FIG. 1;

FIG. 3 is a side view of the apparatus shown in FIG. 1, shown from the other side; and FIG. 4 is a sectional view at section lines B—B of FIG. 1, also showing a wearer's ear.

DETAILED DESCRIPTION OF THE PREFERRED EMBODIMENTS

Reference will now be made to FIGS. 1 through 4, which show various views of the ear covering apparatus 20. The ear covering apparatus 20 comprises an outer shell 22, which is adapted to fit over a wearer's ear. The outer shell 22 includes a front portion 24, a side portion 26, a top portion 28 and a bottom portion 30. The front portion 24 terminates in an inner edge 32, which is adapted to be in intimate contact with the side of the head of the wearer forward of the ear when the ear covering apparatus 20 is in place. The front portion 24 also connects to the side portion 26, the top portion 28, and the bottom portion 30.

The front portion 24 is designed to deflect wind around past the side, top and bottom portions 26, 28, and 30.

The side portion 26 connects to both the front portion 24, the top portion 28, and the bottom portion 30. The side portion 26 terminates at its rear in a rear edge 34.

The top portion 28 connects to the front and side portions 24 and 26. The top portion 28 terminates at its rear in a rear edge 36 and terminates at its side in an inner edge 38. The bottom portion 30 connects to the front and side portions 24 and 26. The bottom portion 30 terminates at its rear in a rear edge 40 and terminates at its side in an inner edge 42.

The inner edges 32, 38 and 42 of the front, top and bottom portions, respectively, are adapted to be in intimate contact with the side of the head of the wearer when the ear covering apparatus 20 is in place. Such intimate contact precludes the passage of air between the inner edges 32, 38 and 42 and the wearer's head.

The inner edges 32, 38, and 42 are generally joined one to another with inner edge 32 spanning between inner edge 38 and 42, thereby generally forming a contact surface 46 that is shaped to generally surround the front, top and bottom of the ear. This contact surface 46 is adapted to contact the wearer's head around the ear such that the C-shape surrounds the ear and is open toward the back.

The rear edges 34, 36 and 40 of the side, top, and bottom portions 26, 28 and 30 respectively, are generally joined to one another forming the trailing edge 48 of the ear covering apparatus 20. The overall shape of the outer shell, which is defined by the front, side, top and bottom portions 24, 26, 28, and 30, is subtantially concave. When the ear covering apparatus 20 is in place over a wearer's ear 49, a concavity 50 is formed. Sound waves approaching generally from the rear can enter this concavity 50 through a rear opening 52, which is defined by the trailing edge 48 of the ear covering apparatus 20, and also by the portion of the head behind the ear of the wearer.

In the preferred embodiment, the side portion 26 includes a first louver 60 and a second louver 62, with a first slot 64 separating the first louver 60 and second louver 62. Preferably the first slot 64 is orientated vertically. The first louver 60 is bounded at its rear by the first slot 64 thus forming a trailing edge 66. The second louver 62 is bounded at its front by the first slot 64 thus forming a leading edge 68. The second louver 62 is displaced rearwardly and inwardly from said first louver 60.

The manner in which the ear covering apparatus of the present invention works is as follows: As the ear covering apparatus 20 is moved in a forward direction through an air mass, as indicated by arrow 70, the oncoming air is forced outwardly from the head of the wearer by the front portion 24. The air then travels along the front portion 24 and then across the side portion 26. The ear is thereby sheltered from air passing by it, thus precluding the noise that is generated by air passing by an unsheltered ear. It has been found, however, that when the air reaches the trailing edge 48, the generally smooth air flow is disturbed and a volume of turbulent air is created as the air flow separates from the vicinity of the trailing edge 48. There is also a great deal of air noise generated by such also turbulent air flow. It has been found that by inclusion of louvers 60 and 62, the air noise generated as the air flow separates from the vicinity of trailing edge 48 is precluded. It is believed that as the air passes over first and second louvers 60 and 62, and across the opening of the first slot 64, the air flow causes a reduced pressure area in the vicinity of the first slot 64 and thus draws air out of the interior concavity 50 of the ear covering apparatus 20. This causes a reduced pressure area within the concavity 50, which in turn draws surrounding air in from the area to the rear of the ear covering apparatus 20. The air drawn into the concavity 50 comes mainly from the air flow that has just passed the side portion 26 of ear covering apparatus 20. Thus, the air separating from the vicinity of the trailing edge 48 is drawn back into the concavity 50 of the ear covering apparatus 20. This sets up a continuous air flow pattern, thereby inhibiting a volume of turbulent air from being formed. Resultingly, there is no significant air noise generated from the vicinity of the trailing edge 48. An observed consequence of this is better discrimination of sound reaching the ear from behind the wearer.

It has been found that having the first and second louvers 60 and 62 bounding the first slot 64 precludes excessive air noise that is present if only a slot is used with no louvers.

It has also been found that the movement of air through the concavity 50 of the ear covering apparatus 20 has a cooling effect on the ear.

Another factor that also increases the level of the sound at the wearer's ear is that the inner surface 72 of the outer shell 22 is generally shaped so as to reflect sound waves toward the opening of the ear. This concentrates the sound waves at the opening of the ear and thereby amplifies the level of the sound by increasing the sound pressure level. A parabolic shape or a portion thereof, is ideally suited for this apparent sound amplification.

Test results have shown that there is very little difference in the sound amplification qualities between an ear covering apparatus having a louver and one that does not, when there is no air flow to create air noise associated with the non-louvered embodiment.

In the preferred embodiment, there is a mounting lug 80 that extends upwardly from the top portion 28. The mounting lug 80 is adapted to allow the ear covering apparatus 20 to be attached to a helmet or the like. Alternatively, the mounting lug 80 can extend from other areas of ear covering apparatus 20.

It is also contemplated that the ear covering apparatus 20 be held in place over the ear by means such as a headband or be configured into a device similar to a set of ear muffs.

In any event, it is possible that the ear covering apparatus 20 could be worn over just one ear or a pair could be worn, each of course covering one ear.

In an alternative embodiment it is contemplated that the side portion 26 has a second slot that is similar to the first slot 64, and one or two additional louvers that define the second slot. The second slot is generally displaced rearwardly from the first slot.

It is also contemplated that additional slots be included in the side portion 26, as found to be desirable.

In a further alternative embodiment, it is contemplated that the side portion 26 has one or more openings therein that are of a different size, shape and orientation than the first slot 64.

In a still further alternative embodiment, it is contemplated that the ear covering apparatus disclosed herein could be incorporated directly into a helmet or the like.

It is also contemplated that this type of device could be used when riding a motorcycle, sailing a boat, playing hockey or football, or many other types of activities where noise may cause hearing or sound discrimination problems.

Other modifications and alterations may be used in the design and manufacture of the ear covering apparatus of the present invention without departing from the spirit and scope of the accompanying claims.

What is claimed is:

1. An ear covering apparatus intended to improve hearing in a rearward direction, comprising:
   an outer shell having a front portion, a side portion, a top portion, and a bottom portion;
   wherein said front portion is joined to said side, top and bottom portions, and has an inner edge for contacting the side of a wearer's head directly forward of the ear;
   wherein said side portion is joined to said front, top and bottom portions and has a rear edge;
   wherein said top portion is joined to said front and side portions, and said top portion has a rear edge and has an inner edge for contacting the side of a wearer's head,
   wherein said bottom portion is joined to said front and side portions, and said bottom portion has a rear edge and has an inner edge for contacting the side of a wearer's head; and
   wherein said three inner edges of said front, top, and bottom portions are connected one with another and are adapted to fit around a wearer's ear, and wherein said three rear edges of said side, top, and bottom portions are generally joined one to another and form a trailing edge of said ear covering apparatus, said trailing edge defining an opening in the rear of said ear covering apparatus, said opening being generally between said trailing edge and the side of a wearer's head.

2. The ear covering apparatus of claim 1, wherein said side portion includes a first slot therein, said slot being for the purpose of redirection air flow in and around said ear covering apparatus.

3. The ear covering apparatus of claim 1, wherein said side portion includes a first louver and a second louver, said first louver having a trailing edge and being bounded at its trailing edge by said first slot, and said second louver having a leading edge and being bounded at its leading edge by said first slot and wherein said first louver is displaced generally forwardly and outwardly with respect to said second louver such that said trailing edge of said first louver is displaced rearwardly and outwardly of said leading edge of said second louver.

4. The ear covering apparatus of claims 2 or 3, wherein said first slot is oriented vertically.

5. The ear covering apparatus of claims 1, 2, or 3, wherein a mounting lug extends from said outer shell, with said mounting lug being adapted for attachment to a helmet.

6. The ear covering apparatus of claims 1, 2, or 3, wherein a mounting lug extends upwardly from said top portion of said outer shell, with said mounting lug being adapted for attachment to a helmet.

7. The ear covering apparatus of claim 1, wherein said inner edges of said front, top, and bottom portions are covered by a protective cushioning material.

8. The ear covering apparatus of claim 7, wherein said cushioning material is in intimate contact the wearer's head such that passage of air between said cushioning material and said wearer's head is precluded.

9. The ear covering apparatus of claim 1, wherein said outershell is of a parabolic shape so as to reflect sound waves towards a wearer's ear when in place.

10. The ear covering apparatus of claim 1, wherein said side portion further includes a third louver and a fourth louver and a second slot separating said third and fourth louvers.

11. The ear covering apparatus of claim 10, wherein said second slot is displaced rearwardly from said first slot.

12. The ear covering apparatus of claim 11, wherein said side portion also includes a fifth louver and a sixth louver and a third slot separating said fifth and sixth louvers.

13. The ear covering apparatus of claim 12, wherein said third slot is displaced rearwardly from said second slot.

14. In a protective helmet, an ear covering apparatus intended to improve hearing in a rearward direction, comprising:
  an outer shell having a front portion, a side portion, a top portion, and a bottom portion;
  wherein said front portion is joined to said side, top and bottom portions, and has an inner edge for contacting the side of a wearer's head;
  wherein said side portion is joined to said front, top and bottom portions and has a rear edge;
  wherein said top portion is joined to said front and side portions, and said to portion has a rear edge and has an inner edge for contacting the side of a wearer's head;
  wherein said bottom portion is joined to said front and side portions, and said bottom portion has a rear edge and has an inner edge for contacting the side of a wearer's head; and
  wherein said three inner edges of said front, top, and bottom portions are connected one with another and are adapted to fit around a wearer's ear, and wherein said three rear edges of said side, top, and bottom portions are generally joined one to another and form a trailing edge of said ear covering apparatus, said trailing edge defining an opening in the rear of said ear covering apparatus, said opening being generally between said trailing edge and the side of a wearer's head.

* * * * *